US008806948B2

(12) United States Patent
Kahn et al.

(10) Patent No.: US 8,806,948 B2
(45) Date of Patent: Aug. 19, 2014

(54) APPARATUS AND METHOD OF DETECTING DEFECTS IN A RAIL JOINT BAR

(75) Inventors: Jason M. Kahn, Anthem, AZ (US); Jeff Wigh, St. Joseph, MO (US)

(73) Assignee: Herzog Services, Inc., St. Joseph, MO (US)

( * ) Notice: Subject to any disclaimer, the term of this patent is extended or adjusted under 35 U.S.C. 154(b) by 696 days.

(21) Appl. No.: 13/036,450

(22) Filed: Feb. 28, 2011

(65) Prior Publication Data

US 2012/0218868 A1  Aug. 30, 2012

(51) Int. Cl.
| | | |
|---|---|---|
| *G01N 29/265* | (2006.01) | |
| *G01S 15/88* | (2006.01) | |
| *G01S 7/539* | (2006.01) | |
| *G01S 17/87* | (2006.01) | |
| *G01S 17/88* | (2006.01) | |

(52) U.S. Cl.
CPC ...... *G01N 29/265* (2013.01); *G01N 2291/2675* (2013.01); *G01S 15/88* (2013.01); *G01S 7/539* (2013.01); *G01S 17/87* (2013.01); *G01N 2291/2623* (2013.01); *G01S 17/88* (2013.01)
USPC ........................................................ 73/634

(58) Field of Classification Search
USPC ............ 73/634, 633, 636, 618, 619, 620, 649
See application file for complete search history.

(56) References Cited

U.S. PATENT DOCUMENTS

| 4,040,738 A | 8/1977 | Wagner | |
|---|---|---|---|
| 4,178,724 A * | 12/1979 | Bruno ............................ | 451/347 |
| 4,217,782 A | 8/1980 | Pont | |
| 4,662,224 A * | 5/1987 | Turbe .............................. | 73/636 |
| 5,497,662 A | 3/1996 | Dykes | |
| 6,055,862 A | 5/2000 | Martens | |
| 7,036,232 B2 | 5/2006 | Casagrande | |
| 7,054,762 B2 | 5/2006 | Pagano et al. | |
| 7,849,748 B2 | 12/2010 | Havira | |
| 7,882,742 B1 | 2/2011 | Martens | |
| 2002/0099507 A1* | 7/2002 | Clark et al. ...................... | 702/36 |
| 2006/0037511 A1* | 2/2006 | Theurer et al. ................... | 104/2 |
| 2009/0323082 A1* | 12/2009 | Patko et al. .................... | 356/603 |
| 2012/0209549 A1* | 8/2012 | Cox et al. ........................ | 702/61 |

FOREIGN PATENT DOCUMENTS

| DE | 4401020 A1 * | 7/1994 |
|---|---|---|
| EP | 2165915 A2 * | 3/2010 |

* cited by examiner

*Primary Examiner* — Peter Macchiarolo
*Assistant Examiner* — Rose M Miller
(74) *Attorney, Agent, or Firm* — Erickson, Kernell, Derusseau & Kleypas, LLC (57) ABSTRACT

An inspection apparatus for detecting defects in a rail joint bar includes an ultrasonic transducer mounted on an actuator for moving the transducer into and out of engagement with a vertical surface of the head of the joint bar. A laser profile system and an encoder output linear position data corresponding to the position of a joint bar relative to the position of the inspection apparatus. A system controller responsive to the identification of the presence of a joint bar or obstructions, outputs control information to the transducer actuator assembly to position the transducer assembly relative to the joint bar.

18 Claims, 10 Drawing Sheets

APPARATUS AND METHOD OF DETECTING DEFECTS IN A RAIL JOINT BAR

FIELD

The present invention relates generally to an apparatus for and method of detecting defects in a rail joint bar and, more particularly, to a mobile apparatus for and method of performing nondestructive-type testing using ultrasonic transducers to detect flaws and defects in a rail joint bar.

BACKGROUND

The United States Federal Railroad Administration has published statistics which indicate that train accidents caused by track failures including rail, joint bars and anchoring resulted in approximately 2700 derailments from 1992 to 2002. The primary cause of these track failures is a transverse defect and fissure running perpendicular to the rail running direction in the rail and rail bar joint.

A pair of rail joint bars holds the two ends of a rail in place and act as a bridge between the rail ends. The rail joint bars prevent lateral and vertical movement of the rail ends and permit longitudinal movement of the rails to accommodate expansion and contraction. Bolts extending through holes in the joint bars and the rail ends secure the rail ends together. Rail joint bars are typically 24 or 36 inches long with four or six bolt holes, respectively.

Various methods of rail inspection include magnetic, contact, ultrasonic and video. One such video system is the Automated Optical Joint Bar Inspection System developed by ENSCO, Inc. in cooperation with the Federal Railroad Administration.

One problem with video inspection systems is the inability to see into the rail joint bar and the area of the rail joint bar hidden under the head of the rail. Further, the most common failure of rail joint bars begins in an area centrally located within the bar. Video systems are also susceptible to false readings because of debris, rust and discoloration or streaks on the joint bar.

Ultrasonic testing of rails is performed with ultrasonic transducers housed in a liquid-filled wheel. The wheel rides along the top of the rail head while the transducers transmit ultrasonic waves into the rail head and receive reflected waves from the rail head. The orientation of the transducers and the wave path are used to identify defects in the rail head and web. However, the wave cannot pass from the rail head into the rail joint bar.

Two such systems are disclosed in U.S. Pat. No. 6,055,862 entitled "Method of and an Apparatus for Detecting, Identifying and Recording the Location of Defects in a Railway Rail," and U.S. Pat. No. 7,882,742 entitled "Apparatus for Detecting, Identifying and Recording the Location of Defects in a Railway Rail," which are hereby incorporated by reference. An ultrasonic joint bar defect detection method and apparatus has been proposed in co-pending application Ser. No. 12/872,460 entitled "Apparatus for and Method of Detecting Defects in a Rail Joint Bar" which is incorporated by reference.

There is a need for a system that can detect defects in joint bars and in particular a system that can identify the presence of a joint bar to activate the defect detection system and that can identify and avoid obstructions to prevent damage to the defect detection system.

SUMMARY

The present invention provides an apparatus for and method of detecting defects in a rail member such as a joint bar. The apparatus includes a pair of opposed liquid-filled transducer roller search units ("RSU") which are repositionable laterally and vertically. Each RSU is protected by a pair of idler rollers one on opposite sides of the RSU to ensure that the RSU is in contact with the head of the rail joint bar and that the ultrasonic transducers contained within the RSU are properly spaced from the joint bar head for measurement.

Pneumatic or hydraulic cylinders or electromechanical devices may be used to reposition the RSUs laterally and vertically to align the RSUs with the joint bar head and to move the wheel assembly away from rail obstructions. A laser profile system utilizes two lasers per rail to collect profile data, which is analyzed to recognize certain features, such as the rail head, the joint bar shoulder and obstructions or hazards. A position sensor is utilized to allow precise placement of the RSUs to test the joint bars. The apparatus is mounted to a carriage assembly which is secured to a rail inspection vehicle.

RSU with embedded ultrasonic transducers pressed against the joint bar head eliminates air gaps and eliminates the negative effects of a rough surface. Higher performance of the RSU and ultrasonic transducers may be attained by wetting the surface of the joint bar head with water to remove debris to improve the surface contact between the RSU and the joint bar head surface.

The transducers are excited to emit an ultrasonic wave which is coupled to the joint bar head. The emitted ultrasonic wave enters the joint bar head. If the wave encounters a defect it is reflected by the defect. The reflected wave is received by the transducer where it is detected as a pulse echo signal. The defect location, size and depth are determined by the depth of penetration of the ultrasonic wave. The depth of penetration is determined by measuring the time from the emission of the ultrasonic wave to the detection of the pulse echo signal. When the ultrasonic wave impinges on a defect such as a crack, the ultrasonic wave is refracted at the discontinuity scattering the ultrasonic wave energy in all directions. The time delay from emission to detection is a function of the dimensions and orientation of the defect and the angle of refraction. By measuring the time delay from the transducer to the defect and back to the transducer, the defect dimensions and orientation may be geometrically determined.

These calculations depend on knowing the beam profiles of the ultrasonic waves that propagate into the joint bar head by controlling the orientation of the transducer head with respect to the joint bar head surface. The angle of refraction within the joint bar head is controlled by the ultrasonic wave's angle of incident relative to an axis normal to the surface of the joint bar head. The angle of incidence is determined according to Snell's Law, which can be mathematically expressed as sin a/sin b=$V_1/V_2$ where a is the angle of incidence, b is the angle of refraction, and $V_1$ and $V_2$ are the ultrasonic wave velocities in the first and second media, respectively.

A challenge in a dynamic and relatively harsh environment of a railroad is identifying a joint bar, determining the height of the head and identifying possible obstructions within an operational envelope to properly place and align the RSUs to engage the surface of the joint bar head for testing, while moving along a railway.

DETAILED DESCRIPTION

As required, detailed embodiments of the present invention are disclosed herein. However, it is to be understood that the disclosed embodiments are merely exemplary of the invention that may be embodied in various and alternative forms. The drawings are not necessarily to scale; some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

Moreover, except where otherwise expressly indicated, all numerical quantities in this description and in the claims are to be understood as modified by the word "about" in describing the broader scope of this invention. Practice within the numerical limits stated is generally preferred. Also, unless expressly stated to the contrary, the description of a group or class of materials as suitable or preferred for a given purpose in connection with the invention implies that mixtures or combinations of any two or more members of the group or class may be equally suitable or preferred.

Figure 1:
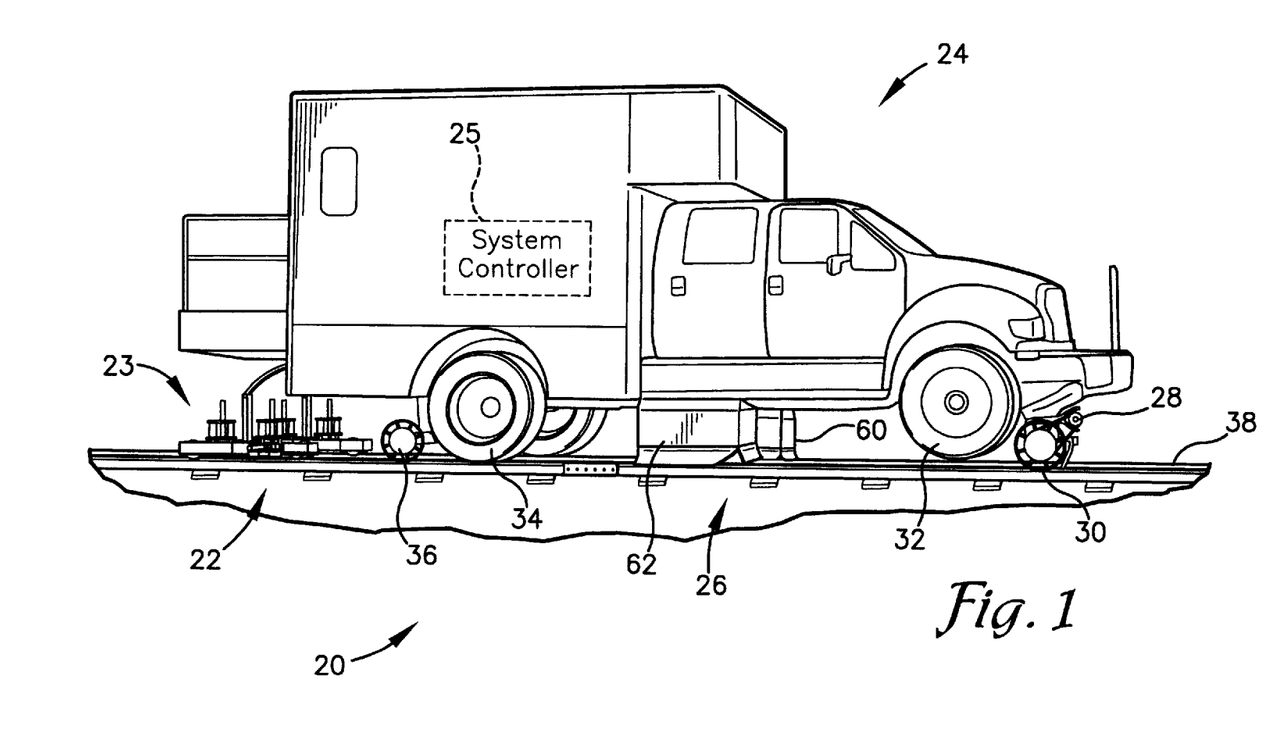
FIG. 1 is an illustration of a test vehicle with a joint bar inspection apparatus of the present invention mounted thereto.
Figure 2:
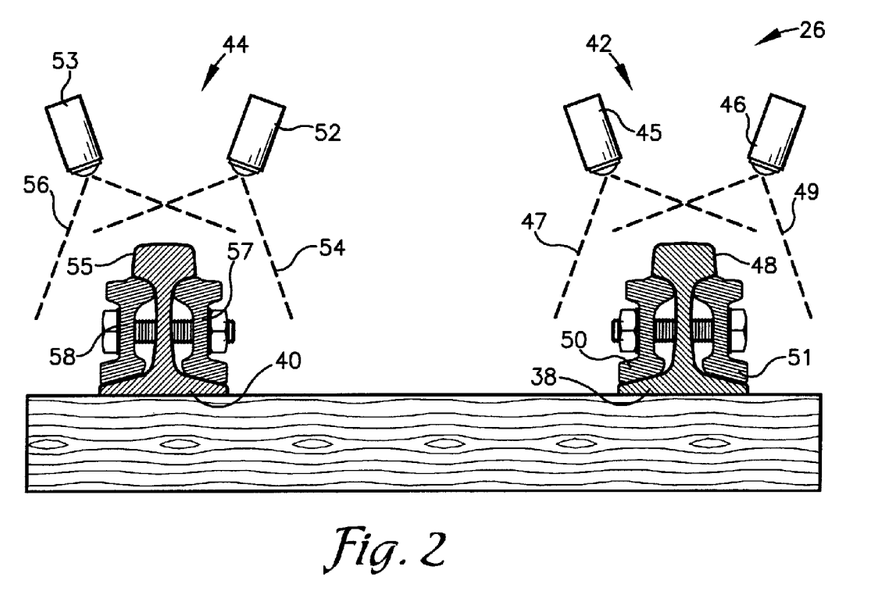
FIG. 2 is a diagrammatic illustration of the laser profiler system.
Figure 3:
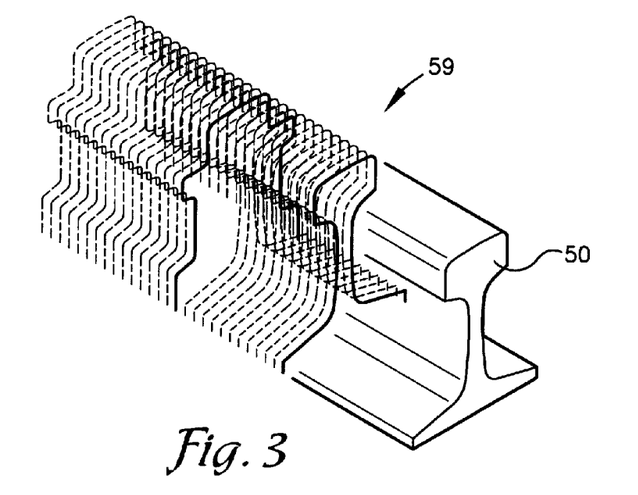
FIG. 3 is an illustration of two-dimensional profile data output by the profiler system.

Referring to FIGS. 1-3, a joint bar inspection apparatus is generally indicated by reference numeral 20. The joint bar inspection apparatus includes a carriage 22 supporting test assemblies 23 mounted behind a test vehicle 24, a laser profile system 26 mounted under the test vehicle 24, and an encoder 28 mounted to a front flanged rail wheel 30, which are coupled to a control system 25.

The test vehicle 24 includes front 32 and rear 34 rubber tires and flanged rail wheels 30 and 36 which serve to keep the test vehicle 24 on the rails 38 and 40 when in a hi-rail configuration. Carriage 22 and the flanged rail wheels 30 and 36 are lifted when the test vehicle 24 is driven off the rails 38 and 40.

The encoder 28 outputs position information to the control system 25. The encoder 28 is preferably an absolute rotary encoder that outputs an analog or digified signal as the rail wheel 30 rotates. The signal from the absolute rotary encoder gives an unambiguous position within the travel range without knowledge of any previous position. The encoder 28 outputs a running counter which corresponds to the rotation of the rail wheel 30 which in turn corresponds to the position of the test vehicle 24.

The laser profiler system 26 includes two pairs 42 and 44 of laser transceivers, each of which is directed at rails 38 and 40, respectively. Laser pair 42 includes a gauge side laser transceiver 45 and a field side laser 46 transceiver directed at rail 38. Gauge side laser transceiver 45 scans the area from the gauge side transceiver 47 of the rail 38 across the rail head 48, which includes joint bar 50. The field side laser 46 scans the area from the field side 49 of the rail 38 across the rail head 48, which includes joint bar 51. Laser pair 44 includes a gauge side laser transceiver 52 and a field side laser transceiver 53. The gauge side laser transceiver 52 scans the area from the gauge side 54 of the rail 40 across the rail head 55, which includes joint bar 57. The field side laser transceiver 53 scans the area from the field side of the rail 40 across the rail head 55, which includes joint bar 57. It should be understood that each laser transceiver may include a laser transmitter and laser receiver, or a laser transmitter and optical receiver such as a camera, as separate components or in combination, for example.

Each laser transceiver scans at a rate of 1000 Hz. The data output from each pair of laser transceivers 42 and 44 is combined to construct a two-dimensional profile or slice 59 of each rail 38 and 40, joint bar 50, 51, 57 and 58 and the surrounding area at a rate of 1,000 times per second. Each pair of lasers 42 and 44 is surrounded by a housing 60 and 62, respectively, each of which encloses the respective laser pair 42 and 44 on the four vertical sides and top to protect the laser system 26 from the environment, to improve the performance of the lasers 45, 46, 52 and 53 in all ambient lighting conditions and to protect the eyes of any individuals located around the test vehicle 24.

Referring to FIGS. 4-9, the carriage assembly 22 includes right 64 and left 66 carriages. The right 64 and left 66 carriages are connected together by a cross member 68, which includes a pneumatic or hydraulic cylinder 70 to adjust the width of the carriage assembly 22 to engage the rails 38 and 40. The right carriage 64 is a mirror image of the left carriage 66 so only the right carriage 64 will be described in detail, it being understood that the same detailed description applies to the left carriage 66.

Figure 4:
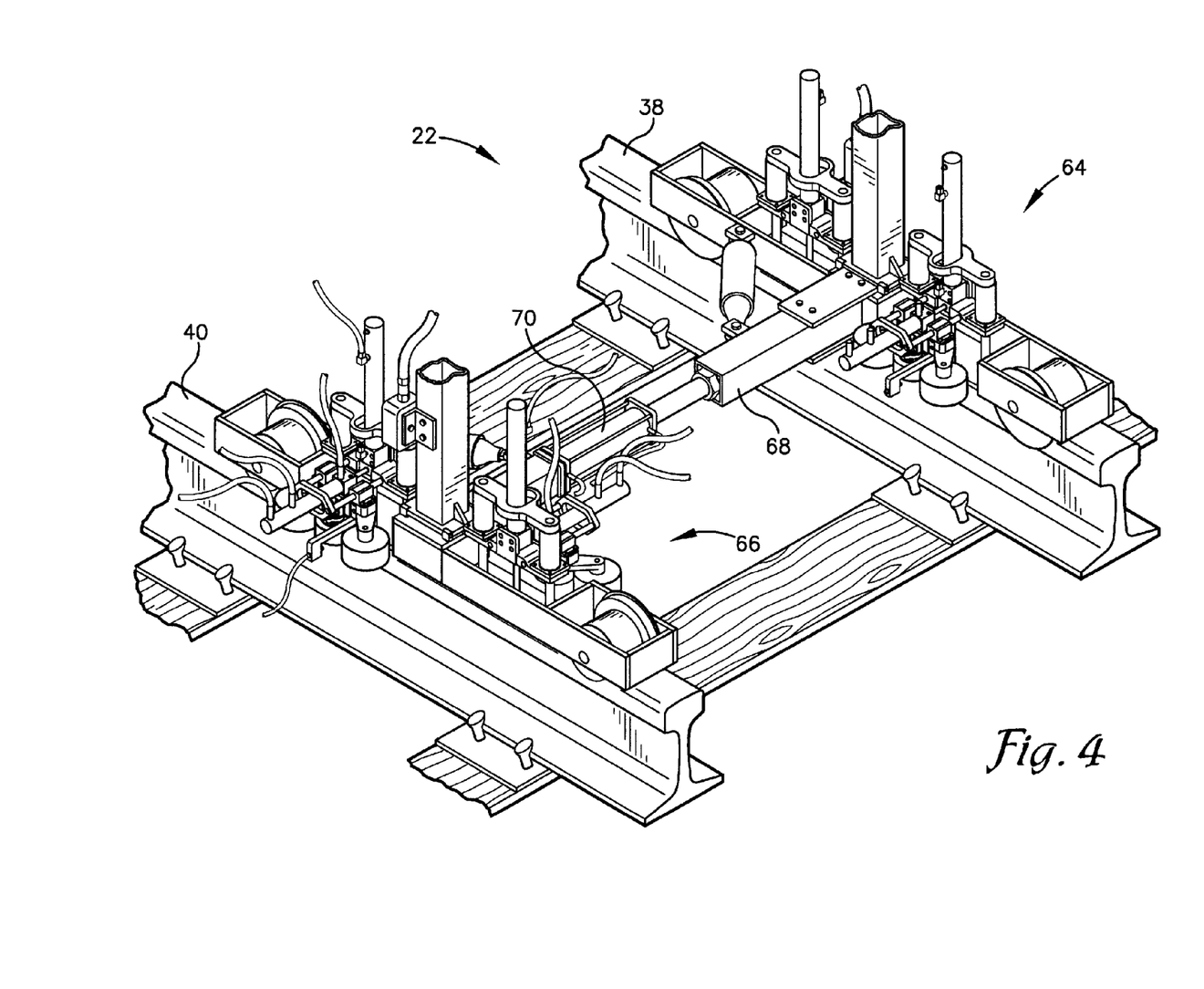
FIG. 4 is a perspective view of a carriage for support of the joint bar inspection assemblies.
Figure 5:
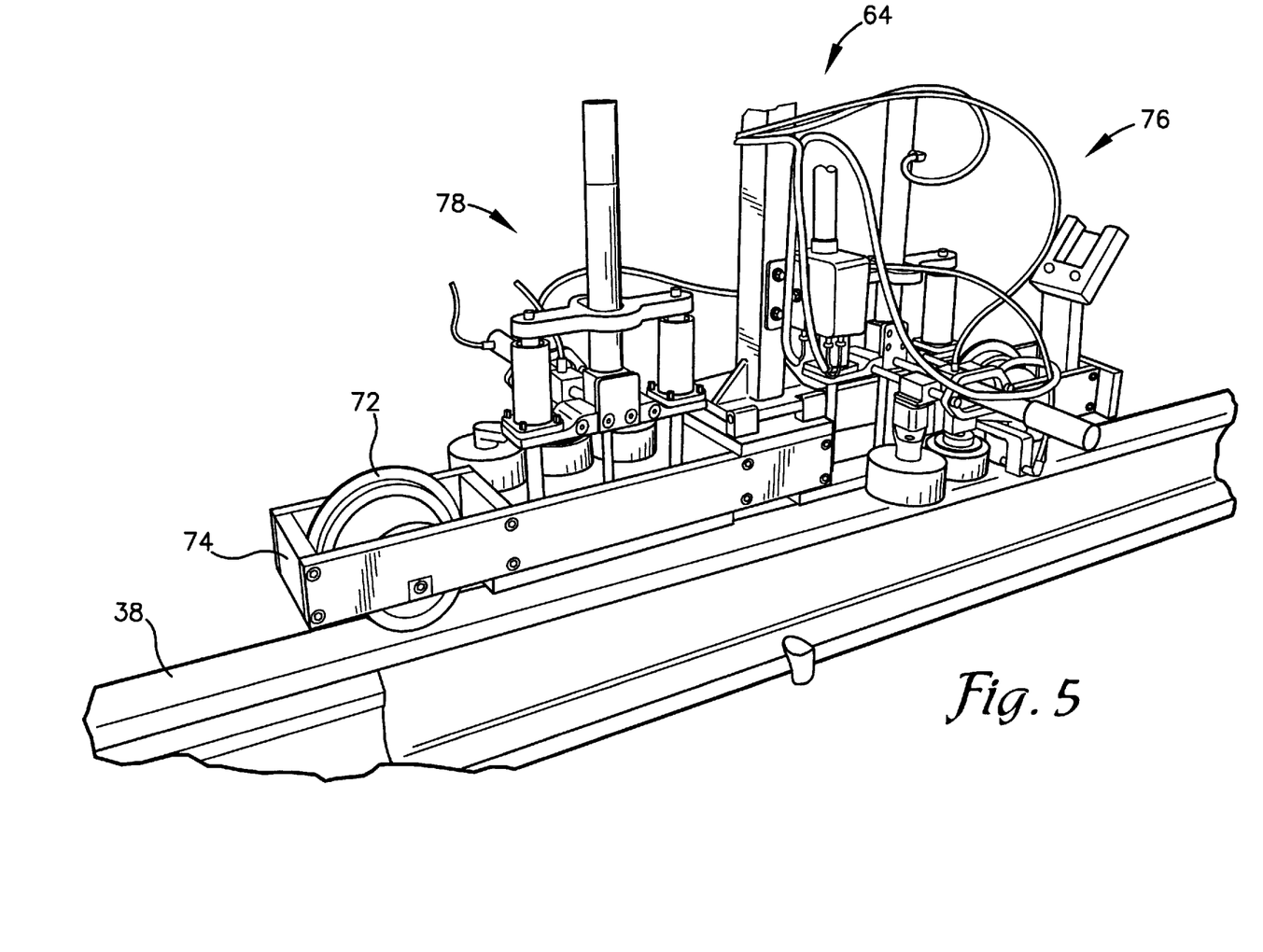
FIG. 5 is a perspective elevation view of one side of the carriage and the mounted joint bar inspection assemblies of FIG. 4.
Figure 6:
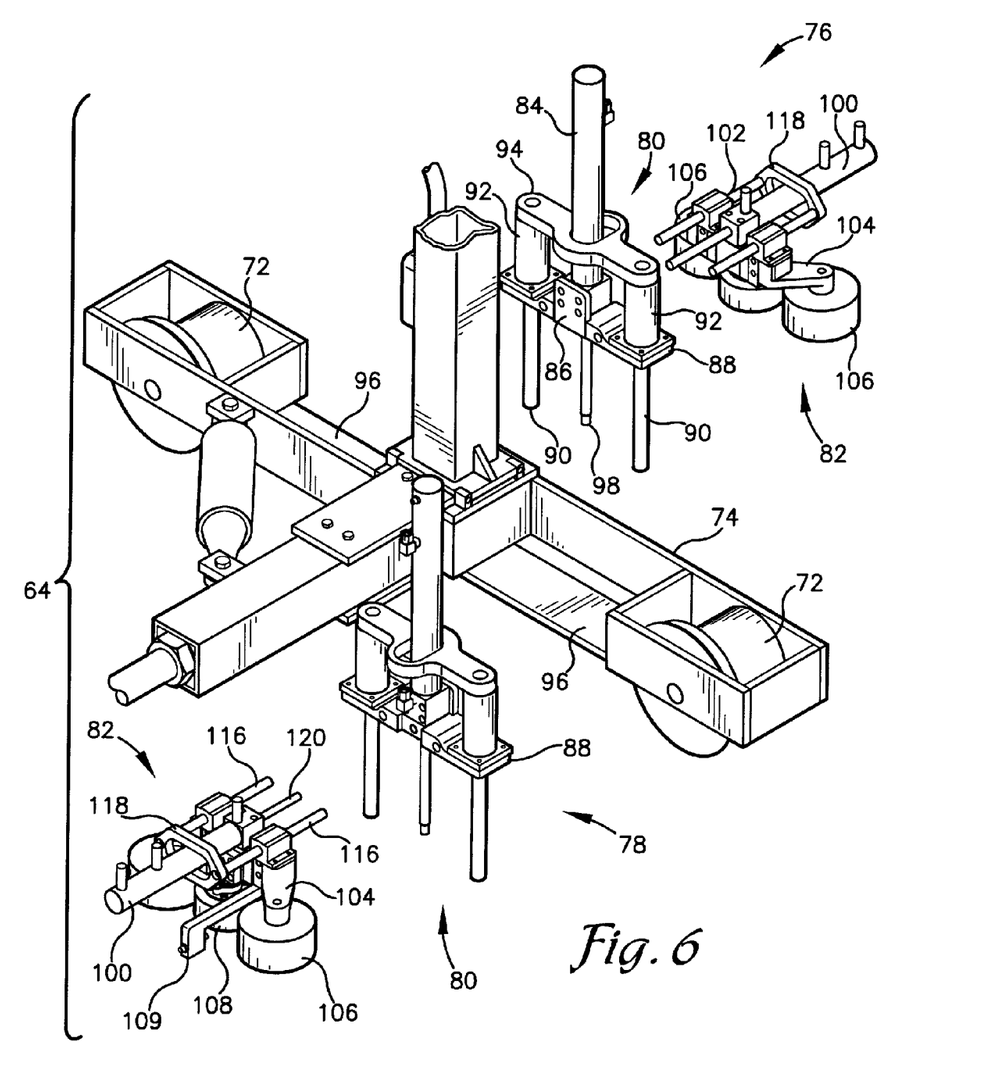
FIG. 6 is an exploded view of one side of the carriage and the mounted joint bar inspection assemblies of FIG. 4.

The right carriage 66 includes a pair of flanged rail wheels 72, which support the carriage 64 on the rail 38. The flanged rail wheels 72 are mounted to a frame 74 to which a field-side wheel assembly 76 and a gauge-side wheel assembly 78 are mounted. Wheel assemblies 76 and 78 are identical and thus like numbers will be used to identify the components and will be identified only for the field-side wheel assembly 76.

Figures 7, 8:
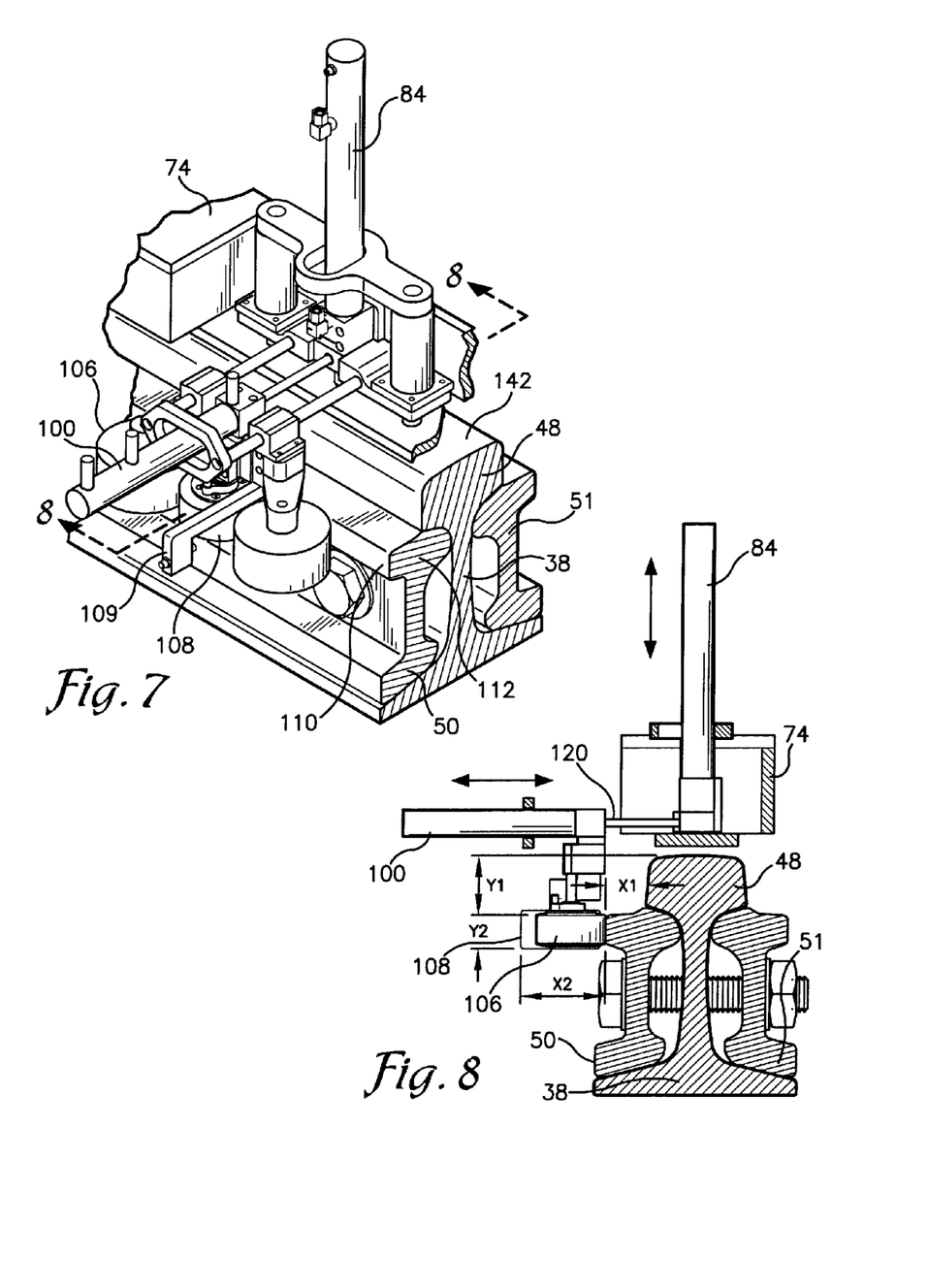
FIG. 7 is a partial sectional view of one side of the carriage and one of the joint bar inspection assemblies.
FIG. 8 is a cross-sectional view of FIG. 7 along line 8-8.
Figure 9:
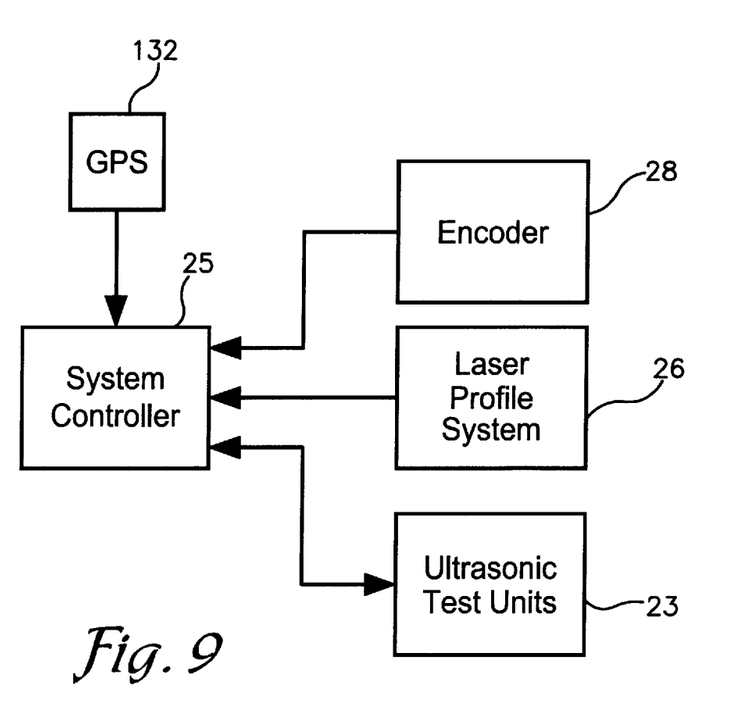
FIG. 9 is a functional block diagram of the rail joint bar apparatus.

Field-side wheel assembly 76 includes a vertical slide assembly 80 and a horizontal slide assembly 82. The vertical slide assembly 80 includes a vertical servopneumatic cylinder 84 fastened to a vertical cylinder mount 86, which is fastened to a slide interface block 88. The slide interface block 88 is slidably coupled to a pair of vertical slide shafts 90, which extend through a pair of bushings 92 and are secured at an upper end to a vertical slide cap 94 and at a lower end to a base 96 of frame 74. A piston rod 98 extends from the vertical servopneumatic cylinder 84 and is secured to the base 96 of frame 74. As the vertical servopneumatic cylinder 84 is actuated, the slide interface block 88 slides up or down in a vertical plane on the vertical slide shafts 90.

The horizontal slide assembly 82 includes a horizontal servopneumatic cylinder 100 fastened to a horizontal cylinder mount 102 which is fastened to a test assembly body 104. The test assembly body 104 includes a pair of idler rollers 106 horizontally mounted on opposite sides of a rolling sensor unit ("RSU") 108. RSU 108 is a liquid-filled wheel, known in the art, which houses one or more ultrasonic transducers mounted at an angle of between 35 degrees and 55 degrees, and more particularly 37.5 degrees and 52.5 degrees relative to the vertical surface 110 of a head 112 of a joint bar 50. The inside surface or inner circumferential edge of the RSU 108 extends beyond the inside surface of the idler rollers 106 so that when the idler rollers 106 are engaged with the vertical surface 110 of the head 112 of the joint bar 50 the RSU 108 is compressed or biased against the vertical surface 110 so that the ultrasonic transducers embedded within the RSU 108 are positioned at a known distance from the vertical surface 110. A liquid spray nozzle 109 may be secured to the test assembly body 104 to spray a liquid such as water on the joint bar head 112 to remove debris and to improve contact of the RSU 108 with the vertical surface 110 of the joint bar head 112.

The test assembly body 104 is slidably coupled to a pair of horizontal slide shafts 116, which are secured at one end to the slide interface block 88 and at the other end to a horizontal slide cap 118. A piston rod 120 extends from the horizontal servopneumatic cylinder 100 with its free end secured to the slide interface block 88. As the horizontal servopneumatic cylinder 100 is actuated, the test assembly body 104 along with the idler rollers 106 and RSU 108 slide back and forth in a horizontal plane on the horizontal slide shafts 116 toward and away from the vertical slide assembly 80.

Referring to FIGS. 1-11, before the test vehicle 24 travels along the pair of rails 38 and 40, the control system 25 is initialized and begins receiving data from the encoder 28, laser profile system 26 a GPS unit 132 and the test units 23. The lasers 42 and 44 scan the rails 38 and 40, respectively, at a rate of 1000 Hz, providing a two-dimensional "slice" 59 of each rail and surrounding area. As the test vehicle 24 travels along the rails 38 and 40, the encoder 28 provides precise linear position data in the form of a counter. Each count output by the encoder 28 represents a distance traveled by the test vehicle 24. For example, the encoder 28 may have a fixed output of 512 counts per foot, or may have a programmable number of counts per selected unit of distance.

Figure 10:
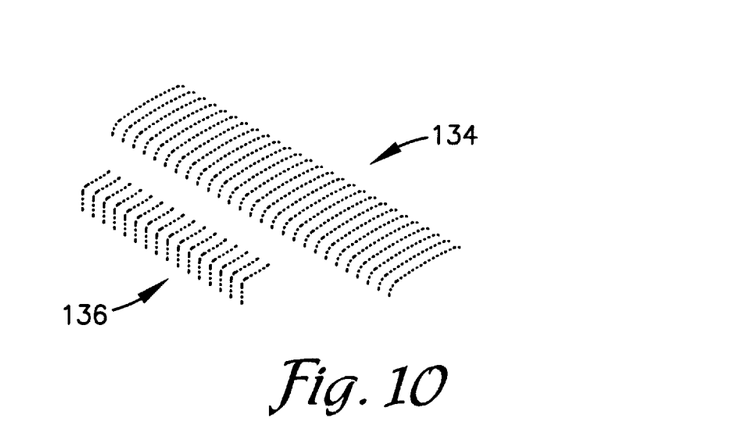
FIG. 10 is an illustration of the analyzed and displayed data from the profile data.

The encoder 28 count is stored along with the output of laser profile system 28 and analyzed by the system controller 25 for certain contours and features based on a slice-to-slice 59 comparison. For example, the system controller 25 recognizes a rail head contour 134 and a joint bar shoulder 136, as well as obstructions. For each joint bar shoulder 136 recognized, the system controller 25 calculates the width of the shoulder 138, defined as X1, and the distance the joint bar head 112 is below the upper surface 142 of the rail head 48, defined as Y1. These calculations are derived from range data received from the laser profile system 24 in a manner generally known in the art. These X1 and Y1 values are derived for each side of the rail head 48 (but not shown in FIG. 11). Because the carriage 22 rides on the rail 38, the zero position of the test apparatus 23 is know and only the horizontal and vertical offset of the joint bar shoulder 136 from the zero position need be determined.

Figure 11:
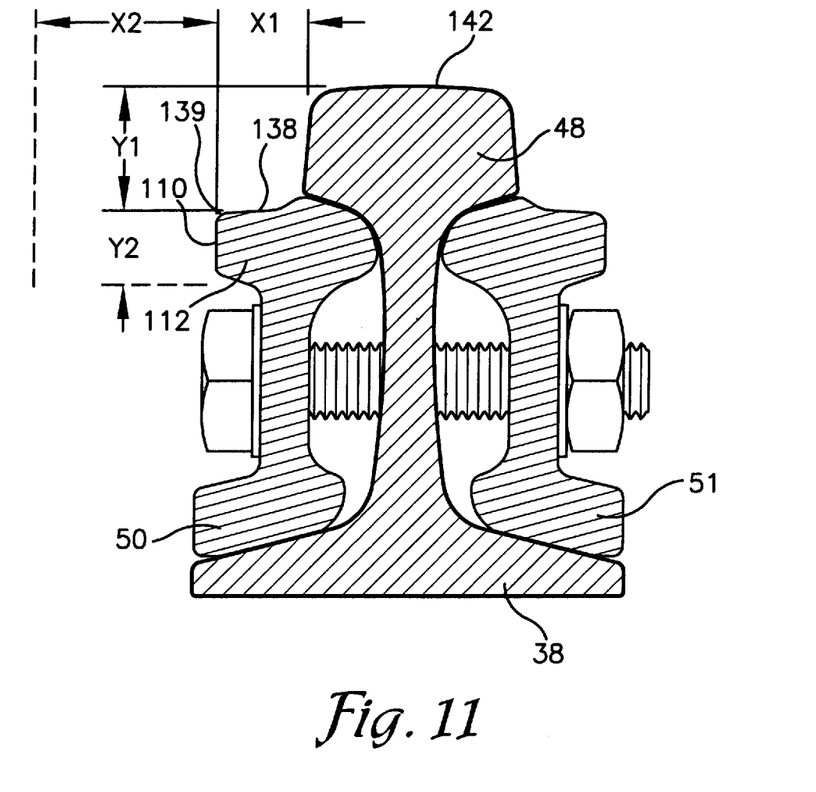
FIG. 11 is a partial diagrammatic illustration of the operational envelope around the rail head and joint bars.

Also calculated is the operational envelope of the test units 23 in order to effectively position the RSU 108 against the surface 110 of the joint bar head 112. The diameter of the RSU 108 is known and height of the joint bar head 112 is derived from that range data. The operational envelope is determined by adding a clearance distance to the RSU diameter or multiplying the RSU diameter by a clearance factor, defined as X1, and by adding a clearance distance to the height of the joint bar head 112 or multiplying the joint bar height by a clearance factor defined as Y2, for example. The operational parameters may be defined by X and Y coordinates (X, Y), where (0, 0) is the stowed position, (X1, Y1) is the outside corner 139 of the joint bar shoulder 138, and (X2, Y2) is the outer envelope of operation. The area defined by X1+X2 and Y1+Y2 determines the operational envelope of the test units 23. This area may be dynamically calculated by the system controller 25 for each side of the rail 38. In the presence of a joint bar 50, obstructions or hazards within this envelope or outside of the envelope but close enough to the envelope to present a risk of contact with any part of the test unit 23 are identified.

Based on the known distance between the lasers 42 and 44 of the laser system 26 and each of the wheel assemblies 76 and 78, precise control and placement of the wheel assemblies 76 and 78 may be accomplished by the system controller 25.

Referring to FIGS. 1-12A and B, the system 20 is initialized before testing begins 198. As the test vehicle 24 travels down the rails 38 and 40, system controller 25 receives data from the laser profile system 26, block 200, and the encoder 28, block 202. The laser profile system 26 outputs four channels of data corresponding to each of the lasers. The encoder data and laser profile data are processed by the system controller 25 and a rail profile (see FIG. 10) is calculated 206 and stored 209. Each rail profile stored is compared to the previous stored rail profile to detect and classify joint bars and other objects based on position, presence and persistence of the features detected 208. The position is a function of identifying an object that matches the profile of a joint bar head and shoulder. The presence is a function of the object being in the expected location next to and below the rail head 48. And persistence is a function of identifying the object a predetermined number of times consecutively.

Figure 12A:
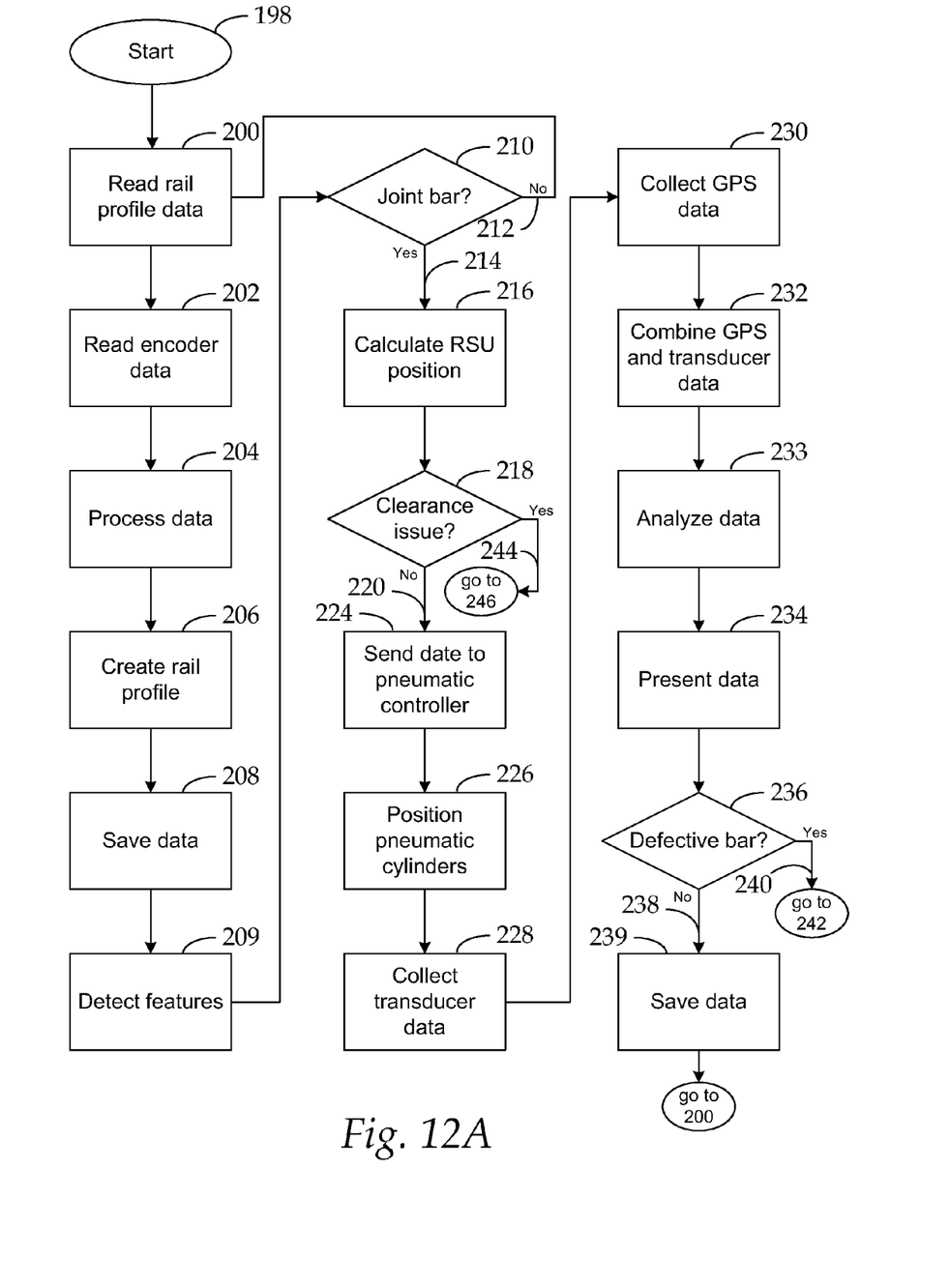
FIGS. 12A and B are a software flowchart illustrating control of the joint bar inspection apparatus.
Figure 12B:
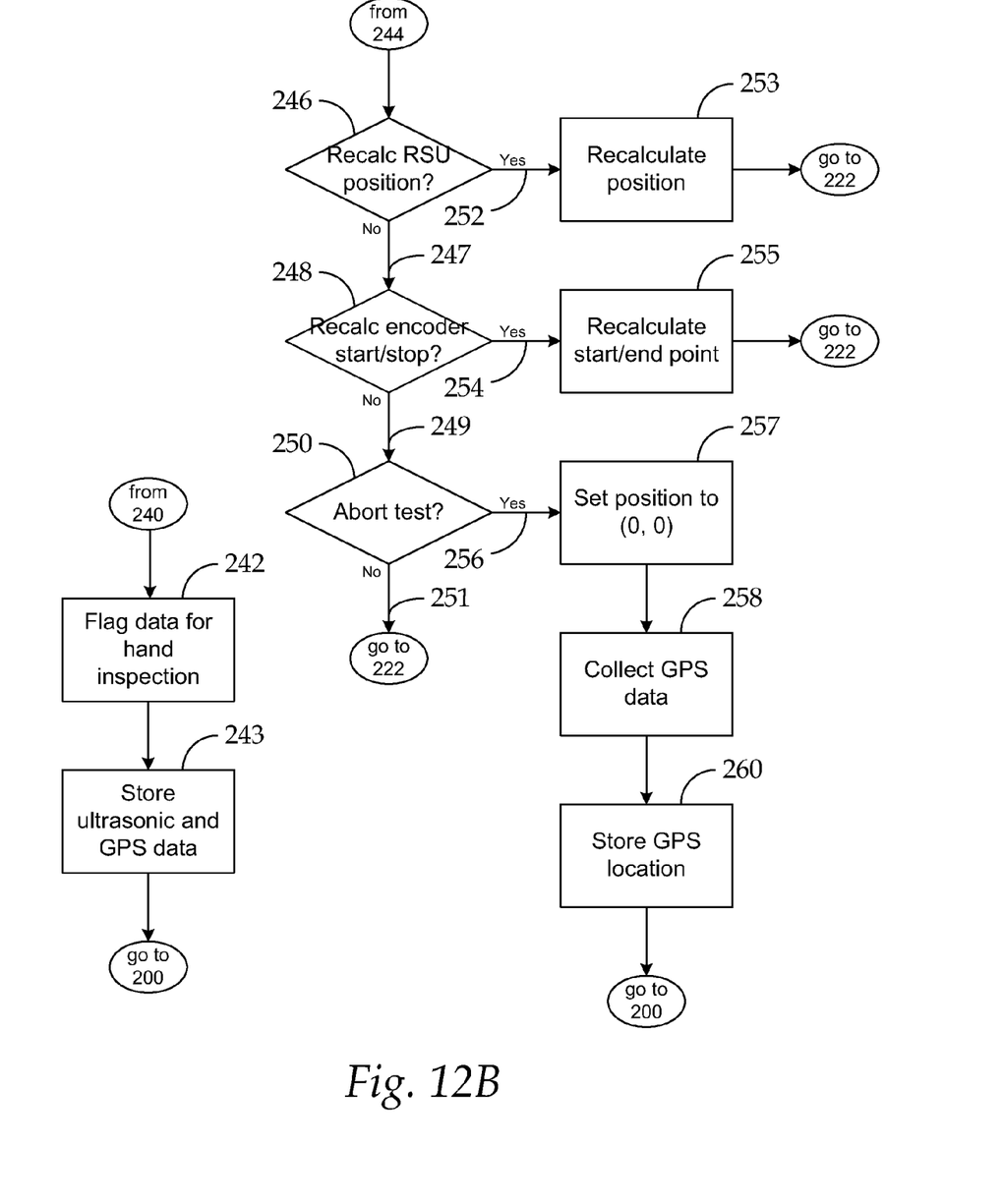

Next, based on the collected data, the system controller 25 determines if a joint bar has been recognized 210. If a joint bar has not been detected 212, then processing returns to block 200. If a joint bar has been detected 214, then the ideal position of the RSU for testing is calculated 216 and a check is made to determine if there are any other objects within the ideal operational envelope of the RSU 218.

If no object has been detected within the operational envelope of the RSU 220, then the test unit 23 is commanded by the computer system 130 to activate the vertical and horizontal servopneumatic cylinders 84 and 100 to move to the calculated position 222 at an encoder 28 count offset by the distance from the laser profile system 26 to the particular wheel assembly 76 or 78. Because the wheel assemblies 76 and 78 are arranged in tandem, the distance from the laser profile system 24 to the field side wheel assembly 76 is different than the distance to the gauge side wheel assembly 78. The position information is received by the servopneumatic controller 224, and the servopneumatic vertical and horizontal cylinders 84 and 100 are positioned 226. The servopneumatic cylinders 84 and 100 provide position feedback to a servopneumatic controller 224 to ensure that they have reached the calculated position. Once in position the ultrasonic transducers in the RSU assembly 108 are energized and data from the ultrasonic transducers 218 is collected and coupled with data output from the GPS receiverl 32 at block 230 by the ultrasonic test hardware and software 232.

The ultrasonic transducer data is analyzed for defects 233 and presented on a display (not shown) to a system operator 234 and checked for defects 236. If no defect(s) are identified 238, the ultrasonic and GPS data are stored 208 with the corresponding profile data and processing returns to block 200. If one or more defects are identified 240, the data is flagged for hand inspection 242 and the ultrasonic and GPS data are stored 243 with the corresponding profile data and processing returns to block 200.

Returning to block 218, if an object has been detected within the operational envelope of the RSU 244 then the controller 25 may determine if the ideal position of the RSU may be adjusted to avoid the object 246, if the test range (i.e., contact range of the RSU 108 with the joint bar head surface 110) may be shortened or modified to avoid the object 248 or if the test should be aborted 250. If the position of the RSU 108 may be adjusted to avoid the hazard 252, then the position is recalculated 253 and processing continues at block 222. A typical situation may include the corner of a bolt or nut head extending into the lower edge of the operational area of the RSU 108 where the vertical positioning of the RSU assembly 108 may be higher than optimal but still within an acceptable range.

If the RSU position does not need to be adjusted 247, then a determination may be made to the start or end position of the RSU 108 may be adjusted to avoid the hazard 248. If the start and/or end point is adjusted 254 and then a different starting and/or end point is calculated 255 and processing returns to block 222. A typical situation may include an obstruction within the RSU operational envelope at the beginning of the joint bar 50 or toward the end of the joint bar 50 relative to the direction of travel of the test vehicle 24. The majority of defects in a joint bar are found near the longitudinal middle where the two sections of rail are joined together.

If the obstruction cannot be practically avoided 259, then a determination is made to whether to abort the test 250. If the test is aborted 256, then the RSU position is set to (0, 0) 257, GPS data is collected 258 and stored 260, and processing returns to block 200.

It is to be understood that while certain now preferred forms of this invention have been illustrated and described, it is not limited thereto except insofar as such limitations are included in the following claims.

Having thus described the invention, what is claimed as new and desired to be secured by Letters Patent is as follows:

1. An inspection apparatus for inspecting a joint bar having a head and an outside vertical surface and mounted on a side of a rail having a head, said apparatus comprising:
   a carriage movably engaging the rail,
   a test assembly secured to said carriage and having an ultrasonic transducer assembly mounted on a transducer actuator assembly,
   a laser profile system having a first laser transceiver directed at the rail,
   a distance measuring device coupled to said inspection apparatus and outputting linear position data corresponding to a relative position of said inspection apparatus on the rail, and
   a system controller coupled to said laser profile system, said distance measuring device and said test assembly, wherein said system controller receives profile data from said laser profile system and linear position data from said distance measuring device which are analyzed to identify the rail head and the presence of a joint bar, said system controller responsive to identification of the presence of the joint bar to determine a vertical and horizontal position of an outside vertical surface of the joint bar relative to the rail head, and
   wherein said system controller outputs control information to said test assembly to actuate said transducer actuator assembly to selectively position said ultrasonic transducer assembly against the outside vertical surface of the joint bar.

2. The apparatus for inspecting a joint bar as in claim 1 wherein said system controller further calculates an operational envelope of said ultrasonic transducer assembly and if an obstruction is identified within said operational envelope of said ultrasonic transducer assembly by said laser profile system, said system controller outputs control information to said transducer actuator assembly to move said ultrasonic transducer assembly to avoid said obstruction.

3. The apparatus for inspecting a joint bar as in claim 1 wherein said distance measuring device comprises an encoder coupled to a rail engaging wheel and outputting linear position information corresponding to rotation of said rail engaging wheel.

4. The apparatus for inspecting a joint bar as in claim 1 further comprising a second laser transceiver directed at the rail.

5. The apparatus for inspecting a joint bar as in claim 4 wherein said first laser transceiver is directed to the gauge-side of the rail and said second laser transceiver is directed to the field-side of the rail.

6. The apparatus for inspecting a joint bar as in claim 1 wherein said transducer actuator assembly includes a servopneumatic cylinder.

7. The apparatus for inspecting a joint bar as in claim 6 wherein said servopneumatic cylinder provides position feedback information to said system controller.

8. An apparatus for inspecting a joint bar having a head and shoulder with an outside vertical surface and mounted on a side of a railroad rail having a head, said apparatus comprising:
   a carriage having at least one wheel for engaging the rail,
   a test assembly secured to said carriage having vertical and horizontal actuator assemblies, and an ultrasonic transducer assembly secured to said horizontal actuator assembly,
   a laser profile system having a first laser transceiver directed at the rail,
   an encoder coupled to a rail engaging wheel and outputting linear position information corresponding to rotation of said rail wheel, and
   a system controller coupled to said laser profile system, said encoder and said test assembly, whereas said system controller receives profile data from said laser profile system and position data from said encoder which are analyzed to identify the rail head, presence of a joint bar and any obstructions proximal the rail,
   whereas said system controller is responsive to identification of said joint bar to determine a horizontal and vertical offset position of said joint bar shoulder, and a start linear position and an end linear position,
   whereas said system controller calculates an operational envelope of said test assembly, and
   whereas said system controller outputs control information to said test assembly to actuate said vertical and horizontal actuators to position said ultrasonic transducer assembly against said outside vertical surface of said joint bar corresponding to said height of said joint bar head.

9. The apparatus of claim 8 wherein if an obstruction is identified within said operational envelope of said test assembly, said system controller outputs control information to said test assembly to avoid said obstruction.

10. The apparatus of claim 9 wherein said control information output to said test assembly to avoid said obstruction includes adjusting said vertical position information to avoid said obstruction.

11. The apparatus of claim 10 wherein said control information output to said test assembly to avoid said obstruction includes linear position information to position said ultrasonic transducer assembly against said outside surface of said joint bar at a linear position after a linear position occupied by said obstruction.

12. The apparatus for inspecting a joint bar as in claim 8 further comprising a second laser transceiver directed at the rail.

13. The apparatus for inspecting a joint bar as in claim 12 wherein said first laser transceiver is directed to the gauge-side of the rail and said second laser transceiver is directed to the field-side of the rail.

14. The apparatus for inspecting a joint bar as in claim 8 wherein said transducer actuator assembly includes a servopneumatic cylinder.

15. The apparatus for inspecting a joint bar as in claim 14 wherein said servopneumatic cylinder provides position feedback information to said system controller.

16. A method of actuating a test assembly to dynamically place an ultrasonic transducer assembly in contact with a surface of a rail member under test comprising:
 identifying the rail member under test,
 determining the orientation of the surface of the rail member under test,
 calculating an operational envelope for the ultrasonic transducer assembly, and
 actuating the test assembly to place said ultrasonic transducer assembly in contact with the surface of the rail member under test.

17. The method as in claim 16 wherein said rail member comprises a joint bar connecting two axially aligned rails.

18. The method as in claim 16 further comprising identifying any obstruction within said operational envelope and wherein said actuating said test assembly step includes avoiding any obstruction identified.

* * * * *